US006506608B2

(12) United States Patent
Mault

(10) Patent No.: US 6,506,608 B2
(45) Date of Patent: *Jan. 14, 2003

(54) METHOD AND APPARATUS FOR RESPIRATORY GAS ANALYSIS EMPLOYING MEASUREMENT OF EXPIRED GAS MASS

(75) Inventor: James R. Mault, Evergreen, CO (US)

(73) Assignee: Healthetech, Inc., Golden, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/933,515

(22) Filed: Aug. 20, 2001

(65) Prior Publication Data

US 2002/0013536 A1 Jan. 31, 2002

Related U.S. Application Data

(63) Continuation of application No. 09/674,897, filed as application No. PCT/US99/17553 on Aug. 3, 1999, now Pat. No. 6,277,645.
(60) Provisional application No. 60/095,092, filed on Aug. 3, 1998.

(51) Int. Cl.$^7$ .............................................. A61B 5/083
(52) U.S. Cl. .......................... 436/133; 436/136; 422/84
(58) Field of Search ................. 436/133, 136, 436/62, 900; 422/84, 98; 600/531, 532, 538

(56) References Cited

U.S. PATENT DOCUMENTS

| 2,630,798 A | 3/1953 | White et al. ............. 128/2.07 |
| 2,826,912 A | 3/1958 | Kritz ......................... 73/194 |
| 2,831,348 A | 4/1958 | Kritz ..................... 73/861.28 |
| 2,838,399 A | 6/1958 | Vogel, Jr. .................... 99/48 |
| 2,869,357 A | 11/1959 | Kritz .......................... 73/32 |

(List continued on next page.)

FOREIGN PATENT DOCUMENTS

| DE | 198 10 476 | 9/1998 |
| EP | 0459647 | 2/1991 |
| EP | 0 712 638 | 12/1995 |
| GB | 2323292 | 9/1998 |
| WO | WO 96/40340 | 12/1996 |

OTHER PUBLICATIONS

Medical Progress Through Technology, vol. 9, No. 1, 1982 Berlin (D), pp. 27–32, R. Salminen et al., "Computerized Breath–By–Breath Analysis of Respiratory Variables During Exercise".

(List continued on next page.)

Primary Examiner—Jeffrey Snay
(74) Attorney, Agent, or Firm—Gifford, Krass, Groh, Sprinkle, Anderson & Citkowski, P.C.

(57) ABSTRACT

The oxygen and carbon dioxide content of expired respiratory gas is determined by measuring the mass and volume of the expired breath. From the composition of the inspired gas which may either be assumed or measured, the mass of the inspired volume may be determined, and since the inspired and expired breaths contain the same mass of nitrogen, the oxygen and carbon dioxide content of the expired breath may be determined. Measurements of temperature and humidity may be required to account for temperature and humidity changes between the inhalation and the exhalation or the inhaled gas may be adjusted in temperature and humidity to equalize the inhaled and exhaled temperature and humidity conditions. The mass and volume of the expiration and the volume mass of the inhalations are determined by an ultrasonic transit time system and a gas density sensor.

26 Claims, 2 Drawing Sheets

U.S. PATENT DOCUMENTS

| | | | | |
|---|---|---|---|---|
| 2,911,825 | A | 11/1959 | Kritz | 73/194 |
| 2,920,012 | A | 1/1960 | Sanders et al. | 167/51.5 |
| 3,213,684 | A | 10/1965 | Seaton et al. | 73/190 |
| 3,220,255 | A | 11/1965 | Scranton et al. | 73/204 |
| 3,250,270 | A | 5/1966 | Bloom | 128/2.07 |
| 3,306,283 | A | 2/1967 | Arp | 128/2.07 |
| 3,523,529 | A | 8/1970 | Kissen | 128/2.07 |
| 3,527,205 | A | 9/1970 | Jones | 128/2.08 |
| 3,681,197 | A | 8/1972 | Smith | 195/63 |
| 3,726,270 | A | 4/1973 | Griffis et al. | 128/2.08 |
| 3,797,480 | A | 3/1974 | Williams | 128/2.08 |
| 3,799,149 | A | 3/1974 | Rummel et al. | 128/2.07 |
| 3,814,091 | A | 6/1974 | Henkin | 128/188 |
| 3,834,375 | A | 9/1974 | Sanctuary et al. | 128/2.07 |
| 3,895,630 | A | 7/1975 | Bachman | 128/2.07 |
| 3,938,551 | A | 2/1976 | Henkin | 137/613 |
| 3,962,917 | A | 6/1976 | Terada | 73/204 |
| 4,003,396 | A | 1/1977 | Fleischmann | 137/83 |
| 4,051,847 | A | 10/1977 | Henkin | 128/145.6 |
| 4,078,554 | A | 3/1978 | Lemaitre et al. | 128/2.08 |
| 4,186,735 | A | 2/1980 | Henneman et al. | 128/201.25 |
| 4,188,946 | A | 2/1980 | Watson et al. | 128/204.22 |
| 4,197,857 | A | 4/1980 | Osborn | 600/531 |
| 4,200,094 | A | 4/1980 | Gedeon et al. | 128/201.13 |
| 4,211,239 | A | 7/1980 | Raemer et al. | 128/716 |
| 4,221,224 | A | 9/1980 | Clark | 128/718 |
| 4,230,108 | A | 10/1980 | Young | |
| 4,341,867 | A | 7/1982 | Johansen | 435/189 |
| 4,359,057 | A | 11/1982 | Manzella | 128/718 |
| 4,368,740 | A | 1/1983 | Binder | 128/718 |
| 4,386,604 | A | 6/1983 | Hershey | 128/718 |
| 4,428,805 | A | 1/1984 | Ogura et al. | 73/861.29 |
| 4,440,177 | A | 4/1984 | Anderson et al. | 600/532 |
| 4,444,201 | A | 4/1984 | Itoh | 128/716 |
| 4,463,764 | A | 8/1984 | Anderson et al. | 600/532 |
| 4,572,208 | A | 2/1986 | Cutler et al. | 128/718 |
| 4,598,700 | A | 7/1986 | Tamm | 128/671 |
| 4,608,995 | A | 9/1986 | Linnarsson et al. | 128/713 |
| 4,619,269 | A | 10/1986 | Cutler et al. | 128/719 |
| 4,648,396 | A | 3/1987 | Raemer | 600/534 |
| 4,658,832 | A | 4/1987 | Brugnoli | 600/532 |
| 4,753,245 | A | 6/1988 | Gedeon | 128/718 |
| 4,756,670 | A | 7/1988 | Arai | 417/43 |
| 4,781,184 | A | 11/1988 | Fife | 128/205.12 |
| 4,796,639 | A | 1/1989 | Snow et al. | 600/532 |
| 4,850,371 | A | 7/1989 | Broadhurst et al. | 600/532 |
| 4,856,531 | A | 8/1989 | Merilainen | 600/532 |
| 4,909,259 | A | 3/1990 | Tehrani | 600/531 |
| 4,914,959 | A | 4/1990 | Mylvaganam et al. | 73/861.28 |
| 4,917,108 | A | 4/1990 | Mault | 128/718 |
| 4,955,946 | A | 9/1990 | Mount et al. | 600/532 |
| 4,986,268 | A | 1/1991 | Tehrani | 128/204 |
| 4,998,018 | A | 3/1991 | Kurahashi et al. | 250/343 |
| 5,022,406 | A | 6/1991 | Tomlinson | 128/719 |
| 5,038,773 | A | 8/1991 | Norlien et al. | 128/205.23 |
| 5,038,792 | A | 8/1991 | Mault | 128/718 |
| 5,042,500 | A | 8/1991 | Norlien et al. | 600/532 |
| 5,042,501 | A | 8/1991 | Kenny et al. | 600/532 |
| 5,060,506 | A | 10/1991 | Douglas | 73/24.1 |
| 5,060,655 | A | 10/1991 | Rudolph | 128/716 |
| 5,060,656 | A | 10/1991 | Howard | 128/718 |
| 5,069,220 | A | 12/1991 | Casparie et al. | 128/719 |
| 5,072,737 | A | 12/1991 | Goulding | 128/718 |
| 5,081,871 | A | 1/1992 | Glaser | 73/863.23 |
| 5,095,900 | A | 3/1992 | Fertig et al. | 128/207.14 |
| 5,095,913 | A | 3/1992 | Yelderman et al. | 128/719 |
| 5,117,674 | A | 6/1992 | Howard | 73/31.07 |
| 5,119,825 | A | 6/1992 | Huhn | 600/529 |
| 5,178,155 | A | 1/1993 | Mault | 128/718 |
| 5,179,958 | A | 1/1993 | Mault | 128/718 |
| 5,214,966 | A | 6/1993 | Delsing | 73/861.28 |
| 5,233,996 | A | 8/1993 | Coleman et al. | 600/529 |
| 5,282,473 | A | 2/1994 | Braig et al. | 600/532 |
| 5,285,794 | A | 2/1994 | Lynch | 128/719 |
| 5,293,875 | A | 3/1994 | Stone | 128/719 |
| 5,299,579 | A | 4/1994 | Gedeon et al. | 600/532 |
| 5,303,712 | A | 4/1994 | Van Duren | 600/529 |
| 5,309,921 | A | 5/1994 | Kisner et al. | 600/532 |
| 5,326,973 | A | 7/1994 | Eckerbom et al. | 250/343 |
| 5,355,879 | A | 10/1994 | Brain | |
| 5,357,972 | A | 10/1994 | Norlien | 128/725 |
| 5,363,857 | A | 11/1994 | Howard | 600/531 |
| 5,398,695 | A | 3/1995 | Anderson et al. | 600/532 |
| 5,402,796 | A | 4/1995 | Packer et al. | 128/719 |
| 5,419,326 | A | 5/1995 | Harnoncourt | 128/660.02 |
| 5,425,374 | A | 6/1995 | Ueda et al. | 600/532 |
| 5,450,193 | A | 9/1995 | Carlsen et al. | 356/301 |
| 5,468,961 | A | 11/1995 | Gradon et al. | 250/345 |
| 5,503,151 | A | 4/1996 | Harnoncourt et al. | 128/660.02 |
| 5,570,697 | A | 11/1996 | Walker et al. | 128/719 |
| 5,632,281 | A | 5/1997 | Rayburn | 128/719 |
| 5,645,071 | A | 7/1997 | Harnoncourt et al. | 128/719 |
| 5,647,370 | A | 7/1997 | Harnoncourt | 128/725 |
| 5,676,132 | A | 10/1997 | Tillotson et al. | 128/204.23 |
| 5,705,735 | A | 1/1998 | Acorn | 73/23.3 |
| 5,728,585 | A | 3/1998 | Yamamori et al. | 436/133 |
| 5,738,106 | A | 4/1998 | Yamamori et al. | 600/532 |
| 5,754,288 | A | 5/1998 | Yamamoto et al. | 356/301 |
| 5,782,772 | A | 7/1998 | Stegmann | 600/520 |
| 5,789,660 | A | 8/1998 | Kofoed et al. | 73/232 |
| 5,796,009 | A | 8/1998 | Delsing | 73/861.28 |
| 5,800,360 | A | 9/1998 | Kisner et al. | 600/532 |
| 5,816,246 | A | 10/1998 | Mirza | 128/726 |
| 5,831,175 | A | 11/1998 | Fletcher-Haynes | 73/861.28 |
| 5,834,626 | A | 11/1998 | DeCastro et al. | 73/23.3 |
| 5,836,300 | A | 11/1998 | Mault | 128/204.23 |
| 5,922,610 | A | 7/1999 | Alving et al. | 436/116 |
| 5,932,812 | A | 8/1999 | Delsing | 73/861.02 |
| 5,957,858 | A | 9/1999 | Michaels et al. | 600/532 |
| 6,010,459 | A | 1/2000 | Silkoff et al. | 600/532 |
| 6,044,843 | A | 4/2000 | O'Neil et al. | 128/204.23 |

OTHER PUBLICATIONS

British Journal Of Anaesthesia, vol. 49,1977 London (GB) pp. 575–587, J. A. Bushman et al. "Closed Circuit Anaesthesia".

IEEE Transactions On Biomedical Engineering, vol. 35, No. 9, Sep. 1988, pp. 653–659, Capek et al., "Noninvasive Measurement of Cardiac Output Using Partial CO2 ReBreathing".

Clinics In Chest Medicine (Review), vol. 10, 1989, pp. 255–264, Heigenhauser et al., "Measurement of Cardiac Output by Carbon Dioxide Rebreathing Methods".

METHOD AND APPARATUS FOR RESPIRATORY GAS ANALYSIS EMPLOYING MEASUREMENT OF EXPIRED GAS MASS

CROSS REFERENCE TO RELATED APPLICATIONS

This application is a continuation of U.S. patent application Ser. No. 09/674,897, filed Nov. 7, 2000 now U.S. Pat. No. 6,277,645, which is a 371 of PCT/US99/17553, filed Aug. 3, 1999, which claims the benefit of U.S. Provisional Patent Application Serial No. 60/095,092, filed Aug. 3, 1998.

FIELD OF THE INVENTION

This invention relates to a method and apparatus for indirect calorimetry employing respiratory gas analysis and more particularly to a method and system which determines the oxygen and/or carbon dioxide content of the expired gas using measurements of mass and volume of the expired gas and mass and volume of the inspired gas as measured by transit time of ultrasonic pulses passed through the gas.

BACKGROUND OF THE INVENTION

I have a number of patents on respiratory calorimeters. Some of these operate by integrating the flow volume of a number of inhalations and exhalations over a period of time and by subtracting the $CO_2$ volume in the exhalation from the integral of the exhaled volume by scrubbing the $CO_2$ and then subtracting the exhaled flow volume less the $CO_2$ volume from the inhaled flow volume to determine oxygen consumption during the period. I also have a pending application that measures both inspired and expired volume and either $O_2$ or $CO_2$ content to determine oxygen consumption. The carbon dioxide scrubber is bulky and requires replenishment after a number of uses. Carbon dioxide or oxygen analyzers are also relatively expensive.

It has previously been proposed to determine the mass of a gas flowing through a conduit by determining the transit time of ultrasonic pulses passed through the gas in a direction having a component along the axis of flow so as to determine the flow rate of the gas, and additionally determining the density of the gas. U.S. Pat. No. 2,911,825 discloses such a system in which the acoustic impedance of the gas is measured to determine the density. U.S. Pat. No. 5,214,966 similarly employs the transit time of ultrasonic pulses to determine the flow rate and determines the density of the flowing gas through measurement of the velocity of sound through the gas. U.S. Pat. No. 5,645,071 uses the transit time of ultrasonic pulses to determine the flow rate and additionally makes temperature measurements which, with the flow rate, allow the determination of mass of the flowing gas. This latter patent also suggests the application of this device to pulmonary function diagnostics and discloses an additional gas analyzing sensor for determining the carbon dioxide and/or oxygen content of the flowing gas on an on-line, real time basis.

It would be desirable to provide a method of analysis which allows the determination of oxygen consumption, carbon dioxide production and related and derived respiratory factors without the need for any gas analyzers, such as $O_2$ and $CO_2$ analyzers. This would result in a low cost, high precision instrument suitable for a wide range of health care applications.

SUMMARY OF THE INVENTION

Accordingly, the present invention is directed toward a method and apparatus for analyzing respiratory gases to determine oxygen consumption for indirect calorimetry purposes as well as $CO_2$ production and related respiratory factors, by measuring the mass and flow volume of expired gas without the need for additional analysis of the oxygen or $CO_2$ content of the expired gas, through use of measurements of the inhaled gas. In its simplest form, in which the constituents of the inhaled gas are known with sufficient precision, as is the case when the subject is breathing ambient air, and the temperature and humidity of the inspired and expired gases are the same as a result of passage through an artificial nose or the like, or are measured or assumed, the $O_2$ and $CO_2$ contents of the exhaled gases may be determined from measurements of the inhaled and exhaled flow volumes and the mass of the exhaled gases. Alternatively, the mass of the inhaled gas will also be measured. The measurements are preferably made by a subject breathing through the apparatus of the present invention for five to ten minutes with the measurements of the inhalations and exhalations being integrated over those periods.

To understand the method of the present invention and the system for implementing it, assume that the subject is breathing ambient air which has a composition of 79% nitrogen, 21% oxygen and 0.03% $CO_2$. By measuring the flow volume of the inhalations over the test period, the inhaled mass may be determined. Assuming that the exhalations are at the same humidity and temperature as the inhalations, from measurements of the integrated mass and flow volume of the exhalations the $CO_2$ and $O_2$ contents of the exhalations may be determined since the nitrogen content of the inhalations and exhalations will be the same, leaving only two unknowns, and after equalization for the differential in volumes between the inhaled gas the exhaled gas, the mass of the exhaled gas will vary linearly as a function of its $CO_2$ and $O_2$ content. The determination of the $O_2$ and $CO_2$ content of the expired volume is possible because $CO_2$ has a substantially higher density than $O_2$ and moles of $O_2$ and $CO_2$ occupy the same volume so that substitution of $CO_2$ in the exhaled gas for $O_2$ in the inhaled gas changes the gas mass but not the volume.

The system of the present invention preferably makes the flow measurements of the inhaled and exhaled volumes with known ultrasonic pulse transit time techniques and determines gas density with measurements such as acoustic impedance, speed of sound, or temperature. The same apparatus can measure the masses and flow volumes of the inhaled and exhaled gases.

BRIEF DESCRIPTION OF THE DRAWINGS

The invention will be further described in conjunction with the accompanying drawings, in which.

DETAILED DESCRIPTION OF THE PREFERRED EMBODIMENTS

Figure 1:
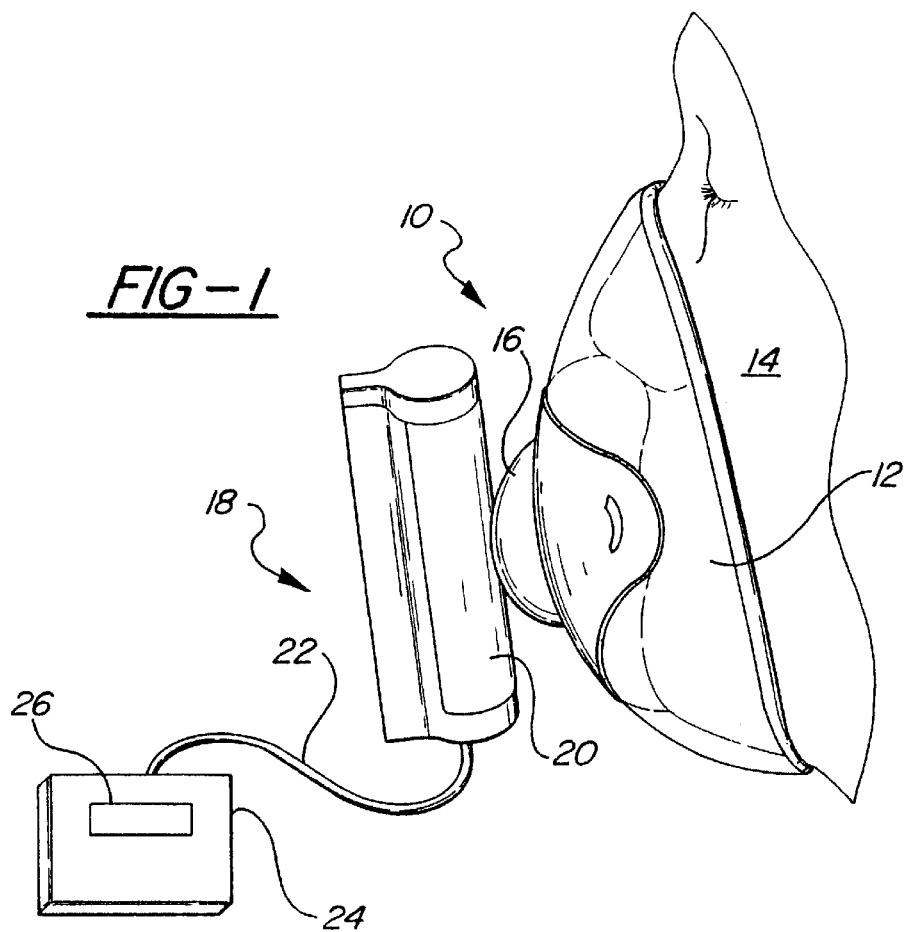
FIG. 1 is a perspective drawing of a preferred embodiment of the invention, being used by a subject to allow determination of the subject's respiratory parameters.

Referring to FIG. 1, a preferred embodiment of the invention comprises a calorimeter, generally indicated at 10, having a mask 12 formed at one end which is adapted to engage the face of a user 14 so as to cover the nose and mouth. The mask connects via a conduit 16 to a test body 18 incorporating a flow tube 20. One end of the flow tube 20 connects to the ambient air. As the user 14 inhales during a breathing test, which may last from two to ten minutes, ambient air is drawn in, passes through the flow tube 20 and to the user 14 through the mask 12. As the user exhales, air moves from the mask 12, through the conduit 16, through the flow tube 20, to the ambient air. In alternative embodiments of the invention, the source and sink for the respiratory gases may be conditioned air as used in forced respiratory apparatus.

A cable 22 connects to the test body 18 and carries electrical signals between the test body and a computation unit 24. The computation unit preferably includes a display 26 which may be switched to display the various results of the test and instructions to the user such as "start test" and "stop test." The flow tube 20 and the mask 12 are preferably formed as a disposable unit so that they may be replaced between uses for hygienic purposes. The balance of the system including the test body 18 and computation unit 24 are preferably reusable. The breath under test only passes through the disposable portions of the system.

Figure 2:
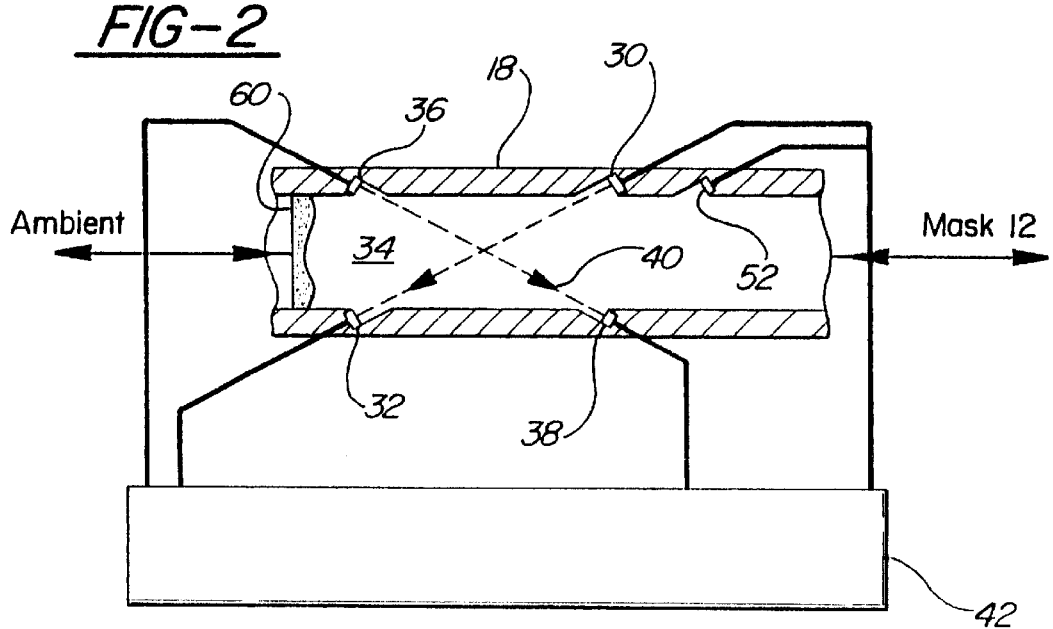
FIG. 2 is a cross sectional view of the flow tube forming part of the preferred embodiment of the invention, illustrating the associated electronics in block form.
Figure 3:
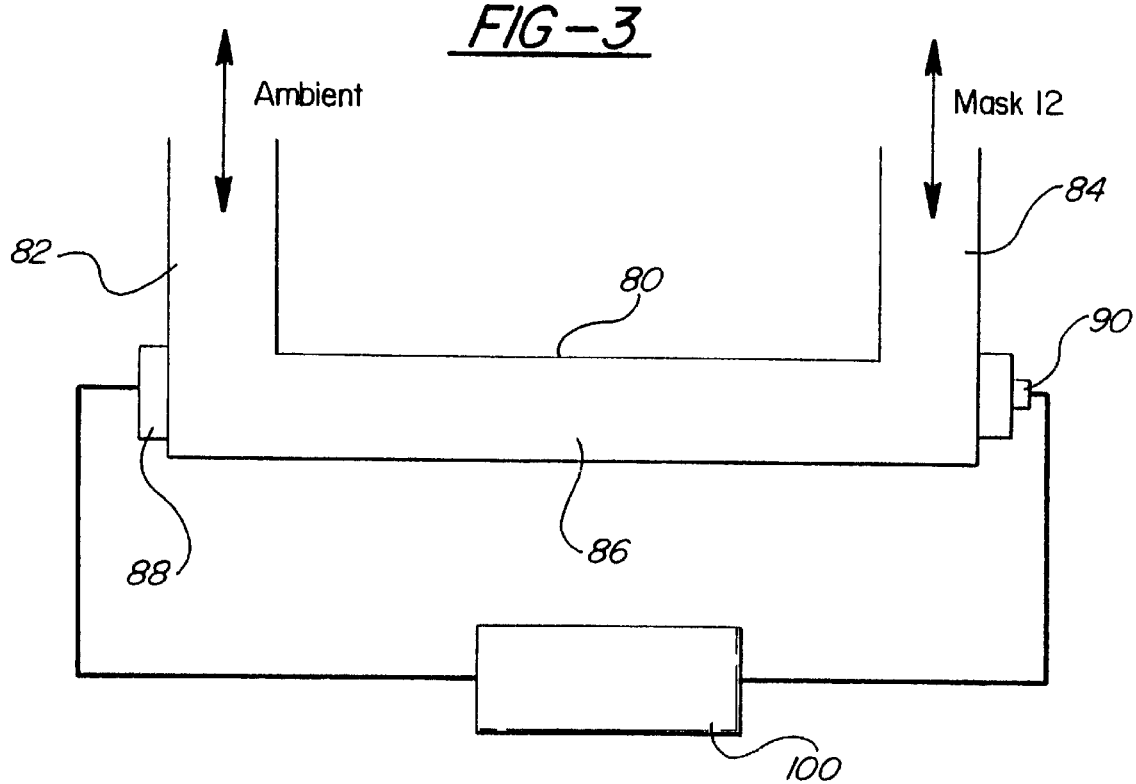
FIG. 3 is a schematic drawing of an alternative embodiment of the invention.

FIG. 2 illustrates the disposable flow tube 18 in cross section. The flow tube and its associated components are of the type illustrated in U.S. Pat. No. 2,911,825 which is operative to calculate the flow rate of the inhaled and exhaled respiratory gases through the tube 18 and to calculate the density of the gases via a determination of the acoustic impedance of the flowing gases. As illustrated in FIG. 2, the left end of the flow tube 18 connects to the atmosphere so that ambient air is drawn into the flow tube when the user inhales and exhaled air is returned to the ambient. The right hand end of the flow tube connects to the mask 12. Thus, inhalations pass through the tube to the right and exhalations pass through the tube 18 to the left.

A pair of piezoelectric crystals 30 and 32 are mounted on opposite sides of the flow tube 18 at an angle to the central axis of the flow tube so that they face one another and ultrasonic pulses may be sent from the crystal 30 to the crystal 32 in the direction of the arrow 34. Similarly, a pair of crystals 36 and 38 are supported on opposite sides of the tube so that they face one another, at an angle to the central axis of the tube, in the direction of the arrow 40. Electrical connections are made from each of the crystals to an electronic control and computation circuit 42 which may be generally of the type illustrated in FIG. 1 of U.S. Pat. No. 2,911,825.

Additionally, another piezoelectric crystal transducer 52 is mounted in a wall of the flow tube 18 so as to contact the gases flowing through the tube. Signals from the transducer 30 are also provided to the computation and control unit 42. Essentially, the control unit controls the crystals 30 and 36 to transmit ultrasonic pulses to the crystals 32 and 38 respectively. The circuitry for generating the pulses and to receive the detected pulses is contained in the unit 42. Since the time of flight of these pulses between the transmitting and receiving crystals is a function of their separation and the rate of flow of gases through the tube, the flow rate may be calculated as a function of the difference between the transit times of the pulses between the two sets of crystals.

The transducer 52 forms one part of a resonance circuit controlled by an oscillator in the unit 42. The frequency of the oscillator is adjusted until the transducer 30 is tuned to series resonance and the voltage drop across the transducer 52 is measured by circuitry contained in the unit 42. This voltage is a measure of the acoustic impedance of the fluid. The density of the fluid is equal to the acoustic impedance divided by the wave propagation velocity through the fluid as fully explained in U.S. Pat. No. 2,869,357. Thus, the computation unit receives signals proportional to the flow rate of gases through the flow tube and the density of those gases and the mass can be calculated. Since the interior diameter of the flow tube 18 is known, the flow volume may be calculated.

The computation unit 42 thus measures the flow volume of the inhalations, the flow volume of the exhalations, and the mass of the exhaled volume.

The unit may incorporate a conventional artificial nose 60 which passes both the inhalations and exhalations and accumulates moisture from the exhalations and generally equalizes the temperature and humidity of the inhalations and exhalations. Alternatively, these temperatures and humidities may be measured or they may be conditioned by active elements such as a thermistor and humidifier.

Assuming that the temperature and humidity of the inhalations and exhalations are equal, the $O_2$ and $CO_2$ composition of the exhalation may easily be computed. The mass of the exhalations is first equalized on the basis of the flow volumes of the inhalations and exhalations. The mass of nitrogen in the inhalations is computed and that mass is subtracted from the mass of the exhaled gas. The remaining mass composed of $O_2$ and $CO_2$ and the mass will vary linearly depending on the proportions of those components so they can be computed or determined from a look-up table. The remaining mass is linearly related to the percentages of $CO_2$ and $O_2$ in the exhalation.

FIG. 2 illustrates the flow tube and associated circuitry of a second embodiment of the invention which uses the method and apparatus disclosed in U.S. Pat. No. 5,214,966 for the determination of the flow velocity and the sound velocity of the respiratory gases passing through the flow tube. The mass of the flowing gas may be calculated using the flow velocity and the sound velocity in the manner set forth in that patent. The flow tube 80 of the second embodiment of the invention is U-shaped with two legs 82 and 84 extending parallel to one another and at right angles to a central connecting section 86. The leg 82 connects the central section 86 to a source and sink for respiratory gases which is preferably the ambient air. The leg 84 connects the other end of the section 86 to the mask 12 illustrated in FIG. 1 or another respiratory connector such a mouthpiece.

Figure 4:
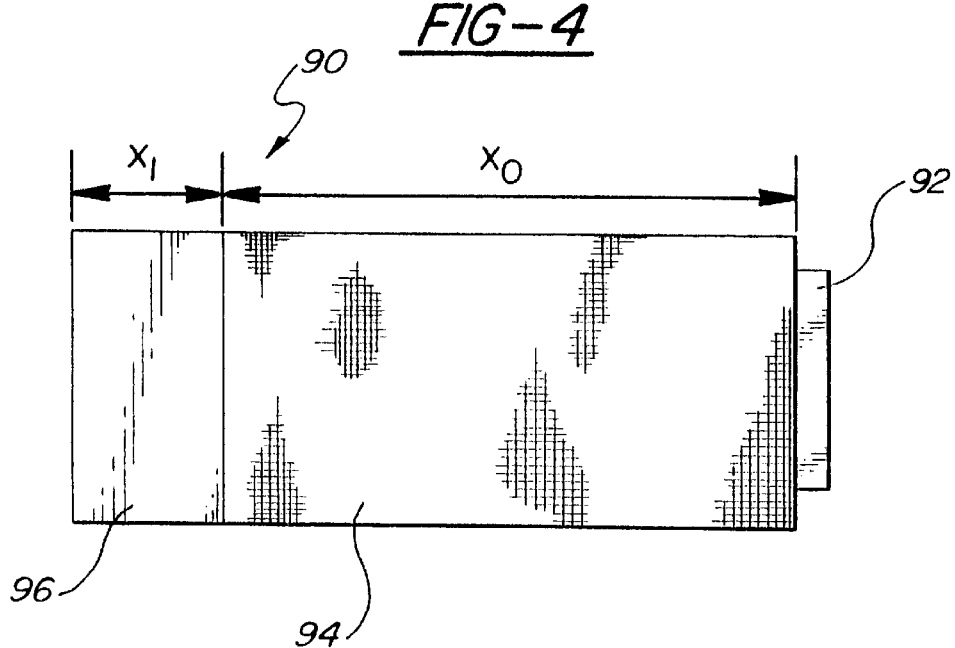
FIG. 4 is a drawing of an ultrasonic transducer capable of measuring the acoustic impedance of the flowing gas.

A first ultrasonic transducer 88 is disposed in the wall of the tube 80 at one end of the connecting section 86 in direct opposition to a second ultrasonic transducer 90 which is disposed at the opposite end so that the two face one another. Each of the two transducers 88 and 90 is formed with a piezoelectric crystal acting as both a transmitter and receiver of ultrasonic pulses. The transducer 90, which is illustrated in detail in FIG. 4, is especially designed for measuring the density of the gases flowing through the flow tube 80. As illustrated in FIG. 2, the transducer 90 consists of a piezoelectric transducer 92, a first block 94 of a material having an acoustic impedance $Z_0$ and a length $X_0$, and a second block 96 having an acoustic impedance $Z_1$ and a length $X_1$. The two blocks 94 and 96 are disposed in such a manner that an ultrasonic pulse transmitted from the crystal 92 will transverse the two blocks 94, 96 before reaching the gas. The first block 94 being disposed between and in contact with the crystal 92 and the second block 96, and the second block 96 is disposed between and in contact with the first block 94 and the gas flowing through the tube 80. The two transducers 88 and 90 are connected to a computation and control unit 100 which contains control and computation electronics. The unit 100 includes sing-around electronic circuitry of a well known type and includes a microprocessor that calculates the flow velocity of gases passing through the section 86 of the flow tube 80.

Simultaneously, the signals from the crystal 90 are used to determine the density of the gas flowing through the section 86 based on the reflection of pulses generated by the transducer 92 from the interface between the crystals 94 and 96, the interface between the crystal 96 and the flowing gas, and the amplitude of those reflections. This is all done in the manner described in U.S. Pat. No. 5,214,966 and will not be repeated. Again, the mass of the exhalations may be calculated from the integrated flow volume density measurements. The flow volume of the inhalation may also be computed and used along with the exhaled volume to analyze the mass reading. The normalized mass will be a function of its complementary $O_2$ and $CO_2$ constituents.

In another embodiment only the expired mass and volume are measured. The expired $O_2$ concentration $[O_2]_e$ and the expired $CO_2$ concentration $[CO_2]_e$ are calculated from the expired mass and volume, and, knowing the inspired $O_2$ concentration $[O_2]_i$, then $V_{O_2}$ is calculated by the following formula:

$$V_{O_2} = \frac{1 - [O_2]_e - [CO_2]_e}{1 - [O_2]_i} \times ([O_2]_i - [O_2]_e) Ve \times k$$

where k is a non-adiabatic correction constant to compensate for the non-ideal nature of the gases, determinable from the van der Waals equation.

The expired volume Ve is a summation of partial volumes attributable to each of the constituent gas making up the expired volume. Since the inhaled oxygen concentration is known or determinable independent of the present invention, the volume of oxygen in the exhalant is related to the exhalant mass change associated with the molar concentrations of oxygen and carbon dioxide relative to inhalant gas. $CO_2$ volume is calculated as:

$$V_{CO_2} = [CO_2]_e \times Ve$$

Where Ve is the total expiration volume.

Having thus described my invention I claim:

1. A method of analyzing exhaled breath produced by a subject over a measurement period, the method comprising:
   determining an exhaled mass of the exhaled breath by integrating a plurality of flow rate determinations and a plurality of density determinations for the exhaled breath passing through a flow tube during the measurement period, wherein the plurality of flow rate determinations for the exhaled breath and the plurality of density determinations for the exhaled breath are determined by passing a plurality of ultrasonic pulses through at least part of the flow tube as the exhaled breath passes therethrough;
   determining an exhaled volume of the exhaled breath by integrating a plurality of flow rate determinations for the exhaled breath passing through the flow tube during the measurement period;
   determining an inhaled nitrogen mass using an inhaled volume of inhaled gases during the measurement period and an inhaled composition of inhaled gases, and determining an exhaled nitrogen mass as equal to the inhaled nitrogen mass;
   subtracting the exhaled nitrogen mass from the exhaled mass of the exhaled breath, so as to determine a mass of residue exhaled gas, wherein the residue exhaled gas is substantially a mixture of carbon dioxide and oxygen; and
   determining a composition of the residue exhaled gas from the exhaled volume of the exhaled gas and the mass of residue exhaled breath.

2. The method of claim 1, wherein the measurement period extends over a plurality of breaths of the subject.

3. The method of claim 1, further comprising the determination of an exhaled carbon dioxide volume from the composition of the residue exhaled gas and the exhaled volume of the exhaled gas.

4. The method of claim 1, further comprising the determination an exhaled oxygen volume from the composition of the residue exhaled gas and the exhaled volume.

5. The method of claim 1, further comprising, the determination of a consumed volume of oxygen by subtracting the exhaled oxygen volume from an inhaled oxygen volume inhaled during the measurement period.

6. The method of claim 1, wherein the inhaled composition is equal to an atmospheric composition comprising substantially of 79% nitrogen and 21% oxygen.

7. The method of claim 1, wherein the inhaled volume is determined by an integration of a plurality of flow rate determinations for inhaled breath passing through the flow tube during the measurement period.

8. The method of claim 1, wherein the inhaled composition is determined by integrating a plurality of flow rate determinations and density determinations for inhaled breath passing through the flow tube during the measurement period.

9. The method of claim 1, wherein the flow path has a cross-sectional are wherein the determination of exhaled mass and the determination of exhaled volume both include a step of multiplying by the cross-sectional area.

10. A method of analyzing the respiration of a subject during a multi-breath test, during which multi-breath test the subject inhales an inhaled volume of inhaled gas having an inhaled gas composition, and exhales an exhaled volume of exhaled gas having an exhaled mass, the method comprising:
    determining the exhaled mass by integrating flow rate data and flow density data acquired during the multi-breath test, wherein the flow rate data are acquired by determining transit times of a plurality of ultrasonic pulses through the exhaled gas, and wherein the flow density data are acquired by determining speeds of sound or acoustic impedances relating to the exhaled gas;
    subtracting a nitrogen mass from the exhaled mass so as to substantially determine a mass of exhaled carbon dioxide and oxygen, wherein the nitrogen mass is determined from the inhaled volume and the inhaled volume composition; and
    determining an exhaled composition from the exhaled volume and the mass of exhaled carbon dioxide and oxygen.

11. The method of claim 10, wherein the flow density data are acquired by determining speeds of sound relating to the exhaled gas.

12. The method of claim 10, wherein the flow density data are acquired by determining acoustic impedances relating to the exhaled gas.

13. The method of claim 10, further comprising the determination an exhaled carbon dioxide volume from the exhaled composition and the exhaled volume.

14. The method of claim 10, further comprising the determination an exhaled oxygen volume from the exhaled composition and the exhaled volume.

15. The method of claim 10, further comprising the determination of a consumed oxygen volume, by subtracting the exhaled oxygen volume from an inhaled oxygen volume.

16. A respiratory analyzer, comprising
   a flow tube, through which inhaled gas and exhaled gas flow;
   at least two ultrasonic transducers, adapted to communicate ultrasonic signals through at least part of the flow tube;
   circuitry adapted to determine a flow velocity of gas passing through the flow tube, wherein the flow velocity is determined using signals received from the ultrasonic transducers;
   means for determining a density of gas passing through the flow tube; and
   a calculation module adapted to determine an exhaled mass from determinations of flow velocity and determinations of density for exhaled gas passing through the flow tube, further to determine an exhaled volume from determinations of flow velocity for exhaled gas passing through the flow tube, further to determine an inhaled nitrogen mass from the inhaled volume and an inhaled gas composition, and to determine the composition of the exhaled gas from the exhaled mass minus the inhaled nitrogen mass.

17. The analyzer of claim 16, wherein the calculation module is further adapted to determine the inhaled volume from flow velocity determinations for inhaled gas passing through the flow tube.

18. The analyzer of claim 16, wherein the calculation module is further adapted to determine an exhaled carbon dioxide volume from the composition of the exhaled gas and the exhaled volume.

19. The analyzer of claim 16, wherein the calculation module is further adapted to determine an exhaled oxygen volume from the composition of the exhaled gas and the exhaled volume.

20. The analyzer of claim 16, wherein the calculation module is further adapted to determine a consumed oxygen volume by subtracting the exhaled oxygen volume from and an inhaled oxygen volume, wherein the inhaled oxygen volume is determined from the inhaled volume of gas and the inhaled gas composition.

21. The analyzer of claim 16, wherein the means for determining a density of gas passing through the flow tube comprises an ultrasonic resonance circuit.

22. The analyzer of claim 16, wherein the means for determining a density of gas passing through the flow tube comprises at least two ultrasonic transducers configured to exchange ultrasonic pulses through at least part of the flow tube.

23. The analyzer of claim 16, further comprising a means for determining temperature.

24. The analyzer of claim 16, further comprising a means for determining humidity.

25. The analyzer of claim 16, wherein the ultrasonic transducers each comprise a piezoelectric crystal in contact with a first block, the first block being in contact with a second block, the second block being in contact with gas in the flow tube, the first and second blocks to having. different acoustic impedances.

26. A respiratory analyzer, for use in a breath test during which a person inhales an inhaled volume of inhaled gas having an inhaled gas of exhaled gas having an exhaled mass, the apparatus comprising:
   a flow path, through which the exhaled gas and the inhaled gas flow;
   a pair of ultrasonic transducers, disposed so that an ultrasonic pulse transmitted by a first ultrasonic transducer is received by a second ultrasonic transducer, and so that the ultrasonic pulse passes through at least part of the flow path;
   circuitry adapted to determine a flow rate and a speed of sound for gas within the flow path, wherein the flow rate and the speed of sound are determined using transit times of a plurality of ultrasonic pulses passed between the pair of ultrasonic transducers; and
   a calculation unit adapted to determine the inhaled volume, the exhaled volume, the exhaled mass, an exhaled nitrogen mass, and an exhaled gas composition,
   wherein the exhaled nitrogen mass is determined from the inhaled volume and the inhaled gas composition, the exhaled gas composition is determined from the exhaled mass minus the exhaled nitrogen mass, and the exhaled mass is determined from a plurality of flow rate determinations and a plurality of speed of sound determinations acquired during times when exhaled breath passes through the flow path.

* * * * *

UNITED STATES PATENT AND TRADEMARK OFFICE
CERTIFICATE OF CORRECTION

PATENT NO. : 6,506,608 B2 Page 1 of 1
DATED : January 14, 2003
INVENTOR(S) : Mault It is certified that error appears in the above-identified patent and that said Letters Patent is hereby corrected as shown below:

Column 1,
Line 11, replace "Aug." with -- September --.

Column 6,
Line 34, replace "are" with -- area --.

Column 8,
Line 16, replace "blocks to" with -- blocks --.
Line 20, after "inhaled gas" insert -- composition, and exhales an exhaled volumn --.

Signed and Sealed this

Twenty-second Day of July, 2003

JAMES E. ROGAN
*Director of the United States Patent and Trademark Office*